United States Patent [19]
Ruiz-Gonzalez

[11] Patent Number: 5,518,009
[45] Date of Patent: May 21, 1996

[54] APPARATUS FOR TREATING COLIC IN INFANTS

[76] Inventor: Susan Ruiz-Gonzalez, 2270 SW. 19th Ter., Miami, Fla. 33145

[21] Appl. No.: 345,603

[22] Filed: Nov. 28, 1994

[51] Int. Cl.⁶ .............................. A61B 19/00; A61F 5/37
[52] U.S. Cl. ................................ 128/869; 128/876
[58] Field of Search ........................ 128/864, 874, 128/875, 876; 600/28; 2/318, 317, 316; 602/19

[56] References Cited

U.S. PATENT DOCUMENTS

| | | | |
|---|---|---|---|
| 4,657,005 | 4/1987 | Williamson | 128/875 |
| 4,873,735 | 10/1989 | Fermaglich | 297/296 |
| 4,941,453 | 7/1990 | Shakas | 600/28 |
| 4,964,401 | 10/1990 | Taigen | 128/876 |
| 5,070,866 | 12/1991 | Alexander | 128/876 |
| 5,178,163 | 1/1993 | Yewer | 128/876 |
| 5,309,926 | 5/1994 | Mayton | 128/876 |
| 5,331,699 | 7/1994 | Patton | 128/876 |

*Primary Examiner*—Michael A. Brown
*Attorney, Agent, or Firm*—Robert M. Downey

[57] ABSTRACT

An apparatus and method for treating colic in infants including an elongate, belt-like device comprised of two-layers of fabric and hook and loop fasteners at opposite ends for securing the device about an infants lower torso. The belt may also include a third layer of rubber or similar air impermeable material, encased between the two layers for trapping heat between the device and the infants body. In treating colic, the belt is wrapped snugly about the infants lower torso, overlying the bellybutton region applying warmth and slight pressure to thereby relieve discomfort.

3 Claims, 1 Drawing Sheet

APPARATUS FOR TREATING COLIC IN INFANTS

BACKGROUND OF THE INVENTION

1. Field of the Invention

The present invention relates to an apparatus and method for treating colic in infants, and more particularly, to an apparatus for treating colic in infants wherein a belt-like device is placed about an infants lower torso.

2. Description of the Related Art

Colic is a severe cramping or gripping pain in the abdomen. In general terms, it is a stomach ache or bellyache, although the stomach is not usually the primary cause of the pain.

Colic is a fairly common condition in infants and often results in irritable crying. For those infants who suffer from colic, it is simply part of the overall development and, in time, the infant will outgrow the condition. Most infants outgrow colic by the time they are three to four months old.

Applicant's invention is designed to relieve the pain and discomfort associated with colic in a manner not previously known by providing a belt-like device which is adapted to be secured about the infant's lower torso. Applicant has discovered that by securing the device snugly about the infant's lower torso, over the bellybutton region, the warmth and slight pressure generated is effective in relieving the discomfort associated with colic.

SUMMARY OF THE INVENTION

The present invention relates to an apparatus and method for treating colic in infants which includes an elongate belt having two layers of fabric attached in overlying relation to one another and fastening means for attaching the opposite ends of the belt to each other so that the belt may be secured about the torso of an infant. The fastening means may include velcro, snaps or other similar fasteners. Alternatively, the belt may also include a center layer, composed of rubber or other similar material, disposed between the two layers in concealed relation therein. In operation, the belt is wrapped around the lower torso of the infant over the bellybutton region and the opposite ends are fastened together to maintain the belt in snug, fitted relation about the lower torso.

With the foregoing in mind, it is an object of the present invention to provide an apparatus for treating colic in infants.

It is another object of the present invention to provide an apparatus for treating colic in infants by applying slight pressure and heat to the infant's stomach and lower torso, particularly in the region of the bellybutton.

It is yet another object of the present invention to provide an apparatus for treating colic in infants which may be adjustably secured about an infant's lower torso in a manner so as to introduce slight pressure and warmth to this area of the body.

It is a further object of the present invention to provide an apparatus for treating colic in infant's which is adjustable to accommodate infant's of different sizes and to provide flexibility to vary the pressure applied to the infant's lower torso.

Various other objects and advantages of the present invention will be readily apparent from the following description.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
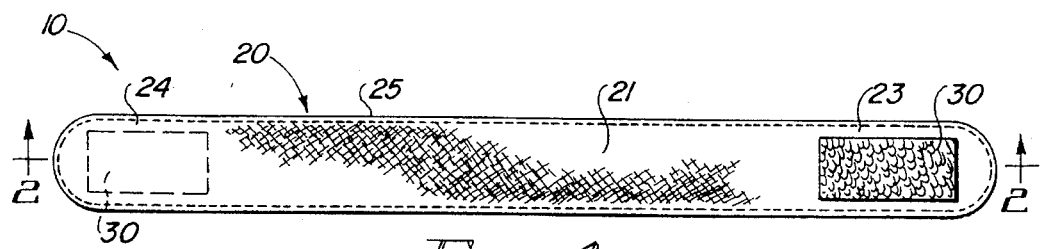
FIG. 1 is a top plan view of a first preferred embodiment of the present invention.
Figure 2:
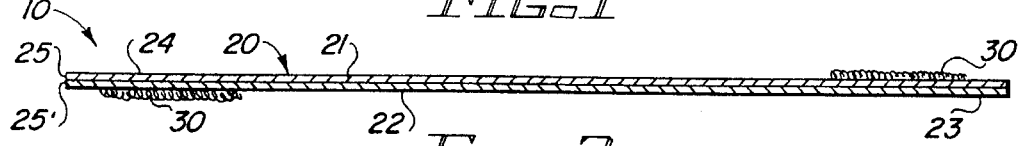
FIG. 2 is a sectional view taken along the line 2—2 of FIG. 1.
Figure 3:
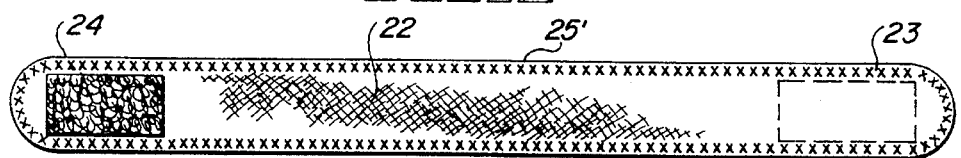
FIG. 3 is a bottom plan view of the device of the present invention.
Figure 4:
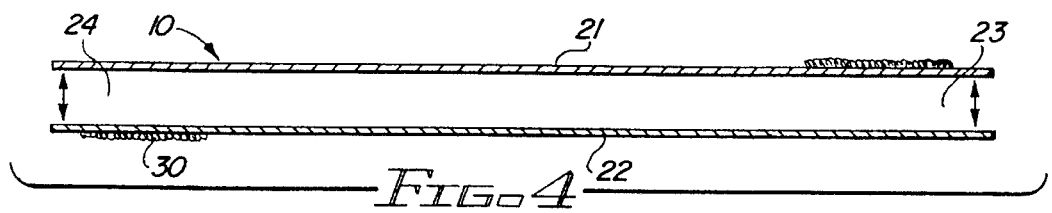
FIG. 4 is an exploded view, in section, illustrating a first and second layer of the embodiment of FIG. 1.
Figure 5:
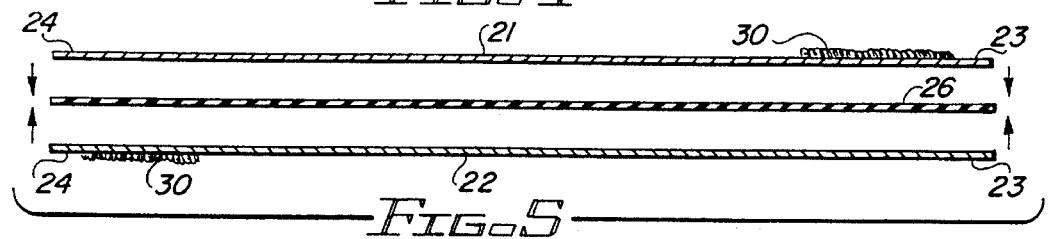
FIG. 5 is an exploded view, in section, illustrating a top layer, middle air impermeable layer and a bottom layer of a second preferred embodiment of the device of the present invention.

With reference to FIGS. 1–7, the present invention is directed to an apparatus for treating colic in infants, generally indicated as 10, including an elongate belt 20 having a top layer 21, a bottom layer 22, a first end zone 23, and an opposite second end zone 24. The top layer 21 and bottom layer 22 may be constructed of cotton fabric, similar to that of a cotton T-shirt, and are disposed in overlying relation to one another. The corresponding, overlaying peripheral edges 25 and 25' of the top layer 21 and bottom layer 22 are stitched together so that the top layer 21 and bottom layer 22 comprise a single elongate belt-like structure 20.

Fastening means 30 such as velcro strips, snaps or loop fasteners are mounted on the top layer 21 of the first end zone 23 and the corresponding mating fastener is mounted on the bottom layer 22 of the opposite second end zone 24 so that the first end zone 23 may be fastened to the opposite second end zone 24, thereby securing the belt 20 about the infant's torso in a manner so as to introduce slight pressure to the bellybutton region.

In a second preferred embodiment of the present invention, the belt 20 further includes a center layer 26 disposed between the top layer 21 and bottom layer 22 in concealed relation therein. The center layer 26 is constructed of rubber or other similar air impermeable material specifically adapted to trap heat between the center layer 26 and the infant's body so as to generate warmth in the region over which the device is secured.

Figure 6:
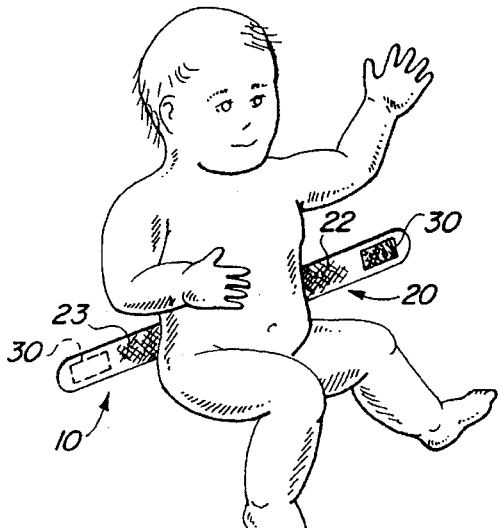
FIG. 6 and 7 are perspective views illustrating the location and manner of securing the device about an infant's lower torso, in accordance with the methods of the present invention.
Figure 7:
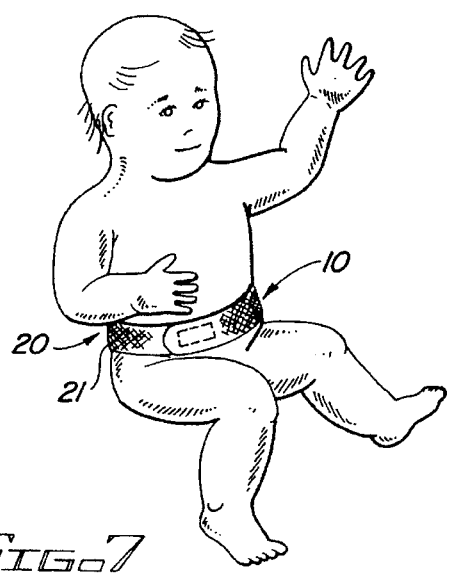

In practice, the apparatus 10 is wrapped around the lower torso of the infant so that the bottom layer 22 overlies the bellybutton region. The first end zone 23 is fastened to the second end zone 24 to maintain the belt 20 in snug, fitted relation about the infant's lower torso and bellybutton region, as seen in FIGS. 6 and 7. The fastening means 30 permits adjustment, if necessary, so that the belt 20 applies slight pressure to the infant's body and traps heat between the belt 20 and bellybutton region, providing warmth in the region and thereby relieving the colicky pain and discomfort.

While the invention has been shown and described in what is considered to be practical embodiments, it is recognized that departures may be made within the spirit and scope of the following claims which, therefore, should within the Doctrine of Equivalents.

Now that the invention has been described,

What is claimed is:

1. A method for treating colic in infants using an elongate belt including top and bottom cotton layers disposed in overlying relation to one another and stitched about their corresponding, overlying peripheral edges, and fastening means for releasably securing a first end zone of the belt to a second end zone of the belt, said method comprising the steps of:

(a) wrapping said belt about said lower torso such that said bottom layer overlies the bellybutton region of the infant in covering relation thereto, (b) securing said first end zone to said opposite second end zone using said fastening means, so that said belt is fitted about said lower torso, (c) adjusting said fastening means so that said belt is maintained in snug, fitted relation about said lower torso, (d) applying pressure to the bellybutton region and the lower torso, (e) trapping heat between said belt and an area of said lower torso over which said belt covers, and (f) applying warmth to the bellybutton region and the lower torso.

2. A method for treating colic in infants as recited in claim 1 wherein said belt further includes an air impermeable center layer disposed between said top layer and said bottom layer in concealed relation therein.

3. A method for treating colic in infants as recited in claim 2 wherein said center layer is constructed of a rubber composition.

* * * * *